United States Patent
Stemmer et al.

(10) Patent No.: US 7,051,286 B1
(45) Date of Patent: May 23, 2006

(54) METHOD FOR ALTERING A PROTOCOL IN A MAGNETIC RESONANCE APPARATUS

(75) Inventors: Alto Stemmer, Erlangen (DE); Rainer Kaim, Obermichelbach (DE); Thomas Kluge, Bamberg (DE)

(73) Assignee: Siemens Aktiengesellschaft, Munich (DE)

(*) Notice: Subject to any disclaimer, the term of this patent is extended or adjusted under 35 U.S.C. 154(b) by 820 days.

(21) Appl. No.: 09/710,903

(22) Filed: Nov. 14, 2000

(51) Int. Cl.
*G06G 9/00* (2006.01)

(52) U.S. Cl. .................. 715/762; 715/771; 715/772; 715/822; 715/823; 715/811; 715/813

(58) Field of Classification Search ............... 345/762, 345/771, 772, 822, 823, 811, 813
See application file for complete search history.

(56) References Cited

U.S. PATENT DOCUMENTS

| | | | |
|---|---|---|---|
| 5,594,849 A * | 1/1997 | Kuc et al. ................ 345/632 |
| 5,606,258 A * | 2/1997 | Hoenninger et al. ........ 324/309 |
| 6,353,445 B1 * | 3/2002 | Babula et al. ............. 345/733 |
| 6,366,834 B1 * | 4/2002 | Hayes et al. .............. 701/1 |

* cited by examiner

*Primary Examiner*—Steven P. Sax
*Assistant Examiner*—Peng Ke
(74) *Attorney, Agent, or Firm*—Schiff Hardin LLP (57) ABSTRACT

In a method for altering a protocol in a magnetic resonance apparatus a first parameter for the protocol and a second parameter for the protocol are displayed in a user interface display presentation. In this display presentation, a range of values for the first parameter is shown, including designation of a first sub-range within the range wherein selection of a value for the first parameter does not modify the second parameter, and designation of a second sub-range wherein selection of a value for the first parameter causes modification of the second parameter. If a value for the first parameter is selected in the second sub-range, the display presentation automatically shows how the value selected for the first parameter will modify the second parameter. The user is given an option, via the user interface to confirm selection of the value for the first parameter, or to reject it.

3 Claims, 6 Drawing Sheets

FIG. 1
(PRIOR ART)

| | | | | |
|---|---|---|---|---|
| Slice group | 1 | FoV read | 300 | [mm] |
| Slices | 2 | FoV phase | 100.0 | [%] |
| Dist. factor | 20 [%] | Slice thickness | 5.0 | [mm] |
| Position | Isocenter | TR | 300 | [ms] |
| Orientation | Transversal | TE | 15 | [ms] |
| Phase enc. dir. | A>>P | Averages | 1 | |
| Phase oversampling | 0 [%] | Concatenations | 1 | |
| | | Filter | None | |
| | | Coil elements | BC | |

Slices: 1 — 2 — 10

FIG. 2
(PRIOR ART)

| | | | | |
|---|---|---|---|---|
| Slice group | 1 | FoV read | 300 | [mm] |
| Slices | 2 | FoV phase | 100.0 | [%] |
| Dist. factor | 20 [%] | Slice thickness | 5.0 | [mm] |
| Position | Isocenter | TR | 300 | [ms] |
| Orientation | Transversal | TE | 15 | [ms] |
| Phase enc. dir. | A>>P | Averages | 1 | |
| Phase oversampling | 0 [%] | Concatenations | 1 | |
| | | Filter | None | |
| | | Coil elements | BC | |

| | | | | |
|---|---|---|---|---|
| Slice group | 1 | FoV read | 300 | [mm] |
| Slices | 12 | FoV phase | 100.0 | [%] |
| Dist. factor | 20 [%] | Slice thickness | 5.0 | [mm] |
| Position | Isocenter | TR | 3000 | [ms] |
| Orientation | Transversal | TE | 15 | [ms] |
| Phase enc. dir. | A>>P | Averages | 1 | |
| Phase oversampling | 0 [%] | Concatenations | 1 | |
| | | Filter | None | |
| | | Coil elements | BC | |

Slices  1 — 12 — 108

FIG. 4
(PRIOR ART)

| | | | | |
|---|---|---|---|---|
| Slice group | 1 | FoV read | 300 | [mm] |
| Slices | 12 | FoV phase | 100.0 | [%] |
| Dist. factor | 20 [%] | Slice thickness | 5.0 | [mm] |
| Position | Isocenter | TR | 332 | [ms] |
| Orientation | Transversal | TE | 15 | [ms] |
| Phase enc. dir. | A>>P | Averages | 1 | |
| Phase oversampling | 0 [%] | Concatenations | 1 | |
| | | Filter | None | |
| | | Coil elements | BC | |

METHOD FOR ALTERING A PROTOCOL IN A MAGNETIC RESONANCE APPARATUS

BACKGROUND OF THE INVENTION

1. Field of the Invention

The present invention is directed to a method for allowing an operator of a magnetic resonance apparatus, such as a magnetic resonance imaging apparatus or a magnetic resonance spectroscopy apparatus, through the operator console for the apparatus.

2. Description of the Prior Art

The pulse sequences utilized in imaging magnetic resonance technology (MRI) and in the magnetic resonance spectroscopy (NMR spectroscopy) are normally parameterizable. Parameters are offered to the operator by means of which the operator selects the anatomy that is of interest (e.g. number, position, orientation of the slices), or influences the contrast between the relevant tissue (e.g. T1/T2 contrast via TR/TE parameters, pre-saturation pulses for fat/water suppression), or selects the resolution depending on the size of the significant objects (e.g. FoV, matrix size, layer thickness), or influences the signal-to-noise ratio of the resulting images (e.g. averages, bandwidth), or controls the measuring time (e.g. TR, TE, concatenations, averages), etc. Generally, the values of these parameters cannot be selected independently of one another. There are numerous dependencies between the individual parameters (for example, TR and the number of the slices), which generally are different for different sequence types. Moreover, the parameter values are subject to further boundary conditions, which, for example, are determined by the efficiency of the utilized hardware (e.g. maximum amplitude and minimum rise time of the gradient system) and the load capability of the patient (e.g. physiological stimulation threshold given rapidly varying magnetic fields).

A difficulty for the dialog system of a MR scanner is to support the user with respect to finding a parameter set (called a protocol), which meets the operator's requirements and which can be implemented with the present hardware.

Conventionally, the user selects a protocol from a set of stored, predetermined protocols, each protocol being optimized for a particular investigation. If parameters must be adapted (normally, this is the case at least for the parameters for selecting the anatomy), only values by means of which the protocol remains intact as a whole, with unchanged values of all other parameters, are offered to the operator/user for each single parameter $P_i$. The advantage of this approach is that the suitability of the protocols for their intended purpose cannot be degraded by the "over-adjustment" by user. As a result of the aforementioned dependency between the parameters, the value range $A_i$ of the parameter $P_i$ generally depends on the value of the other parameters $P_j(j \neq i)$. If the user does not see a desired value offered in the selected protocol, it is theoretically possible to select the desired value subsequent to the modification of one or more other parameters. For this purpose, however, the user needs detailed knowledge about the dependencies between the parameters, which is a disadvantage.

SUMMARY OF THE INVENTION

It is an object of the present invention to provide a method for altering a protocol in a magnetic resonance apparatus which allows an operator to set a parameter to a desired value, which causes at least one other parameter value to change, without the necessity of the operator having to proceed through several steps to determine the effect of setting the parameter to the desired value.

This object is achieved in accordance with the invention in a method for selecting a protocol in a magnetic resonance apparatus wherein the value range $A_i$ of the parameter $P_i$ offered to the user is automatically extended by the measuring system to encompass values that take modifications of other parameters into consideration. The extended adjustment possibilities are offered to the user. If the operator selects a value in the extended value range, the operator is automatically informed (i.e., without the necessity of further operator intervention or action) about the necessary adaptations of the dependent parameters (e.g. by means of a pop-up dialog). In particular, the operator can be given the opportunity to reject the adaptation (and therefore the changed value of parameter $P_i$). It should be noted that a hidden adaptation of the dependent parameters by the system is generally not expedient. Whether the suggestions calculated by the system can be accepted usually depends on the specific examination.

As used herein, the term "magnetic resonance apparatus" encompasses both imaging and spectroscopic systems operating based on nuclear magnetic resonance principles.

The inventive method has several advantages. Operators with less training can utilize the extended adjustment possibilities for the parameter $P_i$. The operation of the measuring system can be learned faster. Trained operators can handle the operation of the measuring system much faster. The operating comfort and workflow is improved. The parameter modifications determined by the measuring system can be optimized with respect to the particular pulse sequence or the particular measuring method, and therefore generally have a better quality than modifications determined by the operator. Particular advantages exist in the case of new pulse sequences/measuring methods with changed dependencies between the individual parameters, or in the case of extension of known methods by new parameters.

Various suggestions can be offered for parameter adaptations, from which the operator can select. The adjustment possibilities of the parameter $P_i$, wherein other parameters must be adapted, can be specifically visualized in the user interface (e.g. by a range display that shows values with and without parameter adaptation in different colors). The inventive method can be directly transferred to all other complex physical measurements with multidimensional, non-cubic parameter spaces (e.g. CT imaging).

DESCRIPTION OF THE PREFERRED EMBODIMENTS

The two immediately following sections concern a typical situation which arises in the preparation of an MR protocol. The operator would like to measure 12 slices, however, the current TR value (300 ms) only allows 10 slices at a maximum. The section "User Action Without Invention" describes the steps necessary for this purpose which would be undertaken by an experienced MR operator working with a conventional system. The section "User Action With the Invention" describes the same scenario with respect to a MRease system (MRease is the new control software of Siemens MR scanning).

The next section describes an exemplary embodiment for a possible software-oriented realization of the inventive method.

Figure 1:
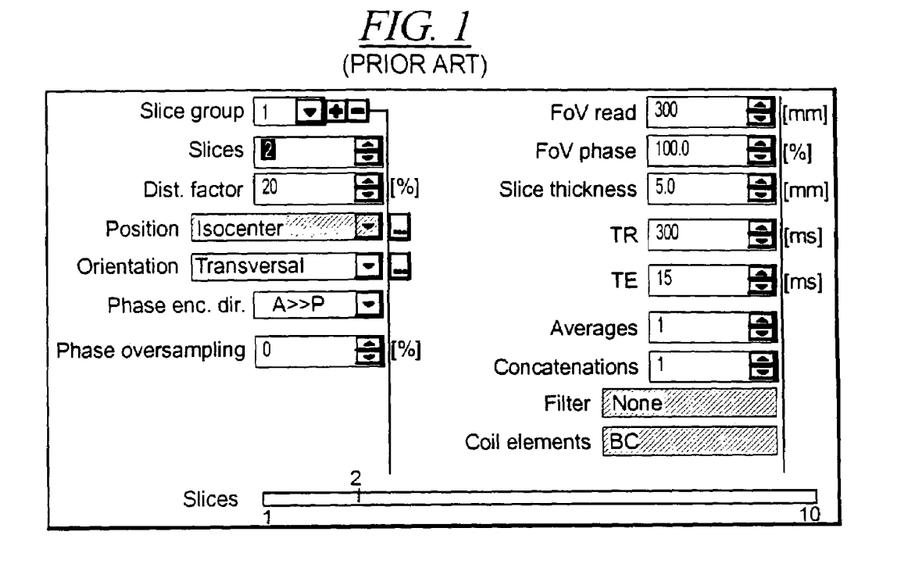
FIG. 1 shows a section of a user interface (operating console display) illustrating a first step for altering a parameter in a magnetic resonance apparatus protocol in a conventional manner.

FIG. 1 shows a section of a conventional user interface in which the measuring parameters can be adjusted. The parameter field "Slices" has been selected by the operator. Subsequently, the value range of the parameter is visualized in the lower part of the user interface. The parameter can be freely set in the range between 1 and 10—without other parameters having to be adapted as a result (known approach). The value desired by the operator (slices=12) is not present. The operator must know that the value of TR must be increased in order to be subsequently able to enter the desired value for "slices".

Figure 2:
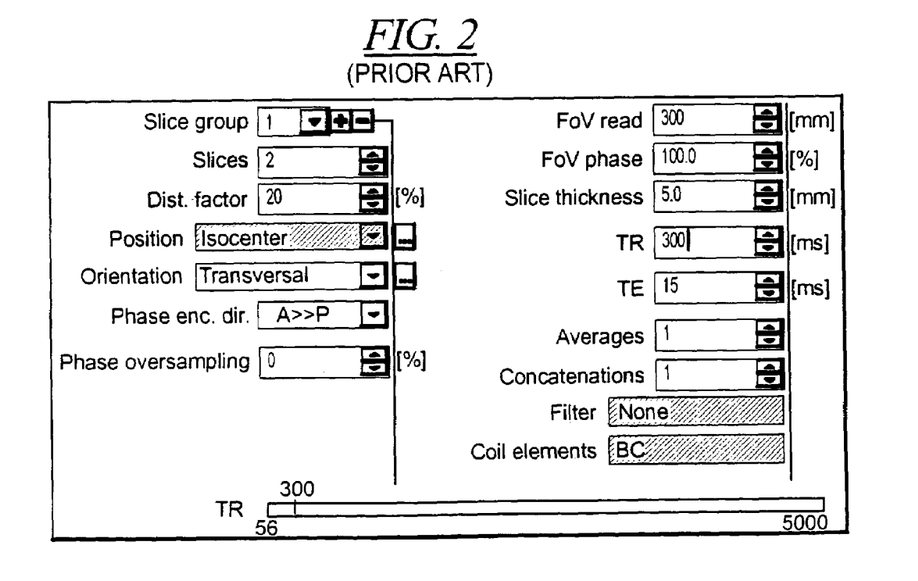
FIG. 2 illustrates the same section of the conventional user interface shown in FIG. 1, in a second step of the conventional procedure.

For this purpose, the operator selects the parameter TR (FIG. 2).

Figure 3:
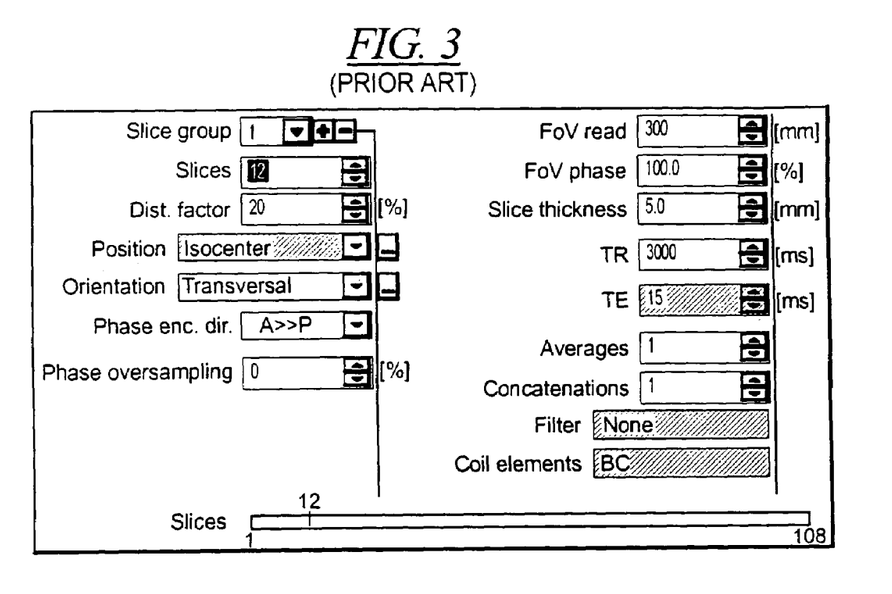
FIG. 3 shows the same section of a conventional user interface as in FIGS. 1 and 2, in a third step of the conventional procedure.

The operator does not know the minimal TR value, which is necessary for increasing the "slices" up to 12 slices. Therefore, the operator initially will select a very high value (here TR=3000 ms) for which the operator is certain that 12 slices are possible. Then, the operator changes over to the parameter field "slices" again (FIG. 3). As can be seen, the TR value is lengthened vis-a-vis FIG. 1.

Figure 4:
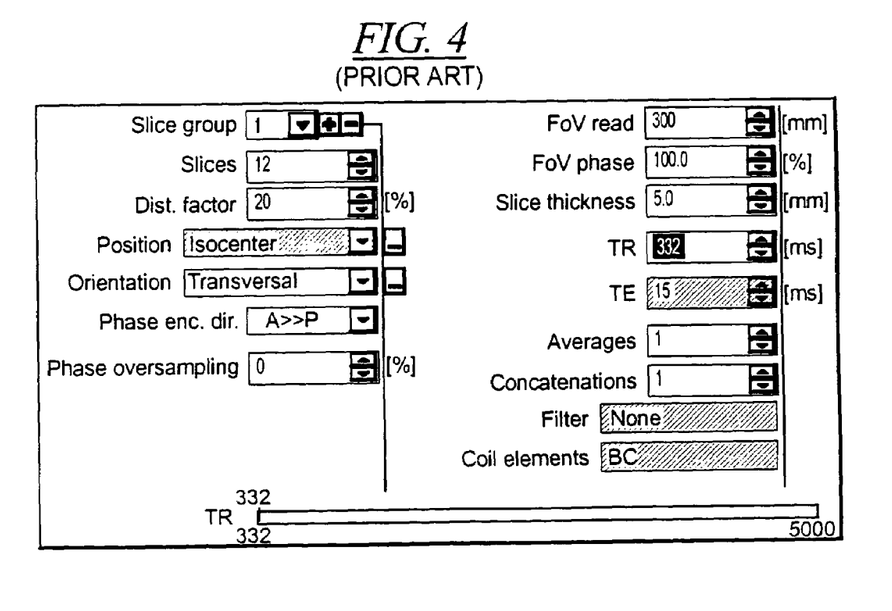
FIG. 4 shows the same section of the conventional user interface as in FIGS. 1, 2 and 3, in a fourth step of the conventional procedure.

Now, the operator could even increase the value of "slices" up to 108. The operator sets the number of the slices to the desired value 12. The operator must now change over to the parameter TR and must set its value to the new minimum (here 332 ms, see FIG. 4). This is necessary, so that the measuring time is not unnecessarily lengthened and so that a similar contrast is received as in the initial protocol.

User Interaction with Invention

Figure 5:
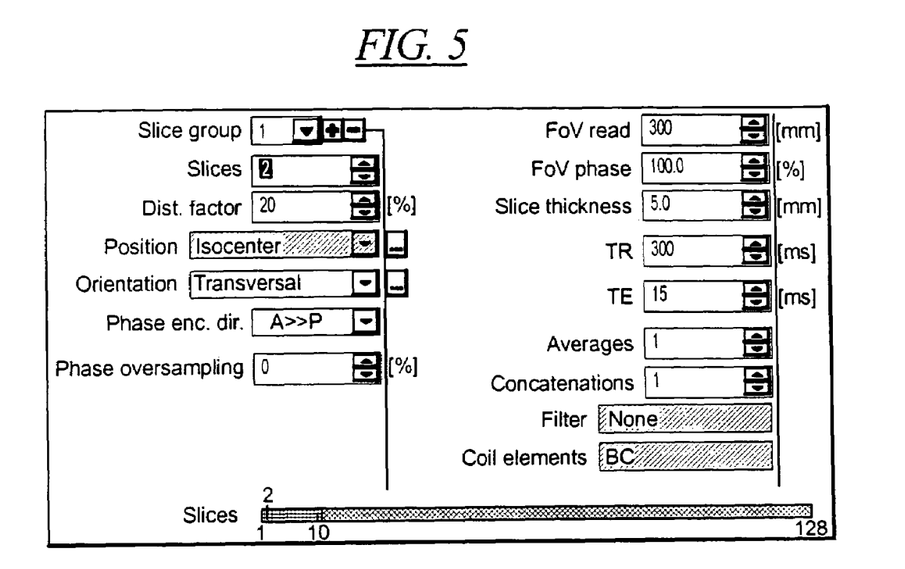
FIG. 5 shows a section of a user interface (operator console display) for altering a protocol in a magnetic resonance apparatus in accordance with the present invention.

FIG. 5 shows a section of the MRease user interface in which the measuring parameters can be adjusted. The parameter field "slices" has been selected by the user. Subsequently, the value range of the parameter is visualized in the lower part of the user interface. The parameter can be freely set in the range between 1 and 10—without other parameters having to be adapted as a result. This parameter range can be for example, green in the range display. On the right side of it (between 11 and 128), the extended value range follows for example, in red.

The operator can directly enter the desired value "slices"=12. As a result of the parameter input in the extended value range, a modal dialog pops up, which informs the operator about the necessary parameter adaptation (here an extension of TR by 32 ms, see FIG. 6).

Figure 6:
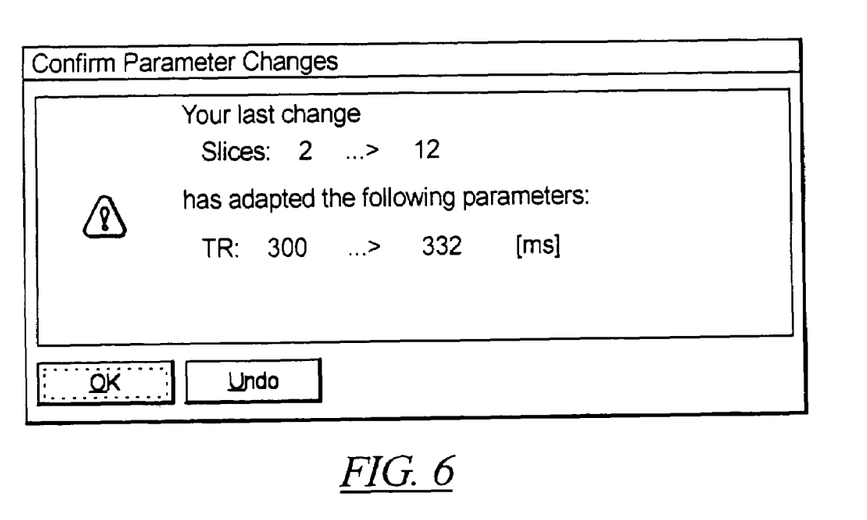
FIG. 6 shows a pop up dialog display which occurs during the execution of the inventive method.

The operator can accept this adaptation (by actuating button command "OK") or can reject it (by actuating "Undo" in the button command). If the operator accepts the adaptation, the operator arrives at the same protocol ("slices" 12, TR=332 ms) as at the end of the scenario "User Interaction Without Invention". In the "undo" case, the original value (slices=2, TR=300 ms) remains.

Realization Details

Figure 7:
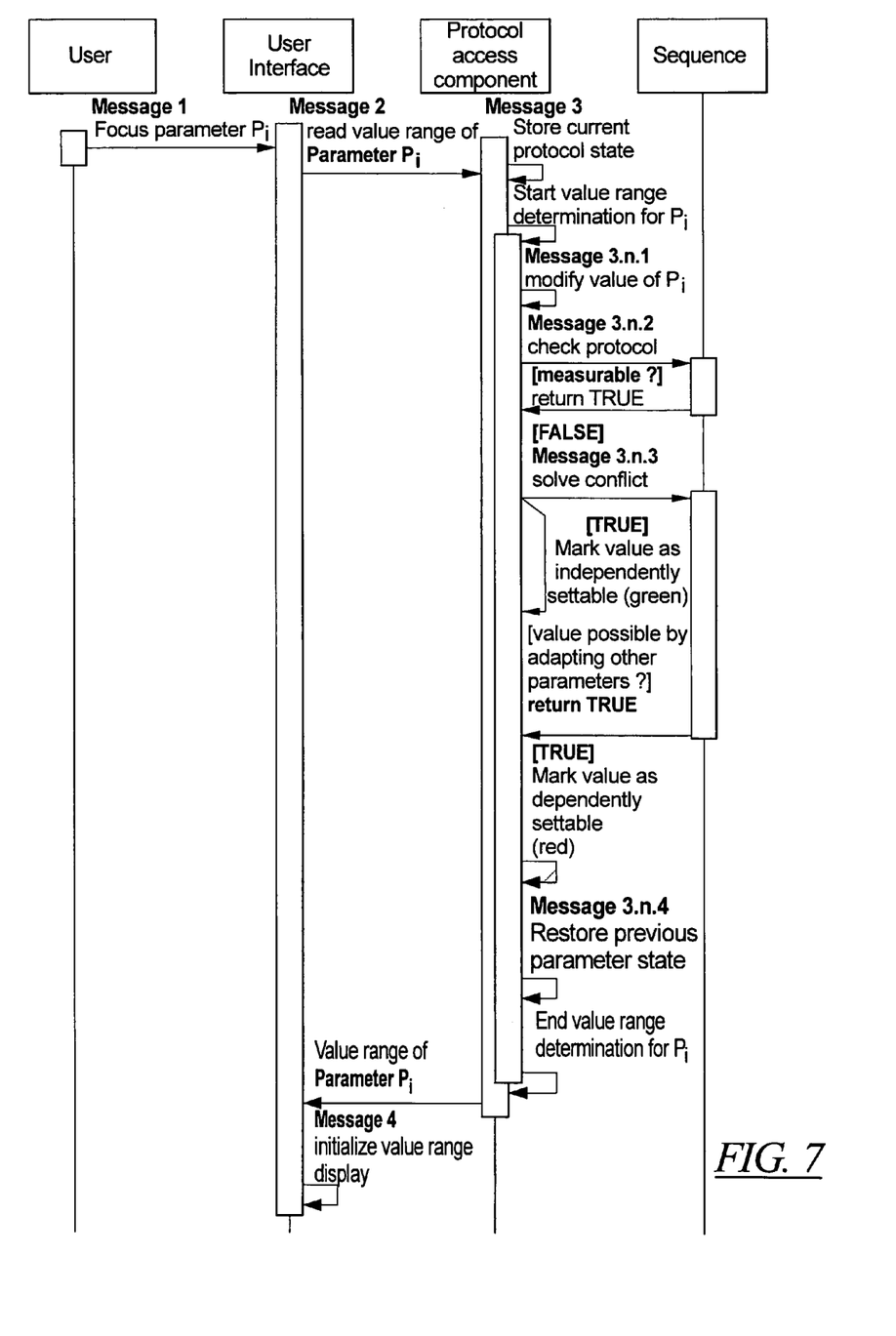
FIGS. 7, 8 and 9 are time diagrams for explaining the interaction of certain components of the magnetic resonance apparatus during execution of the inventive method.
Figure 8:
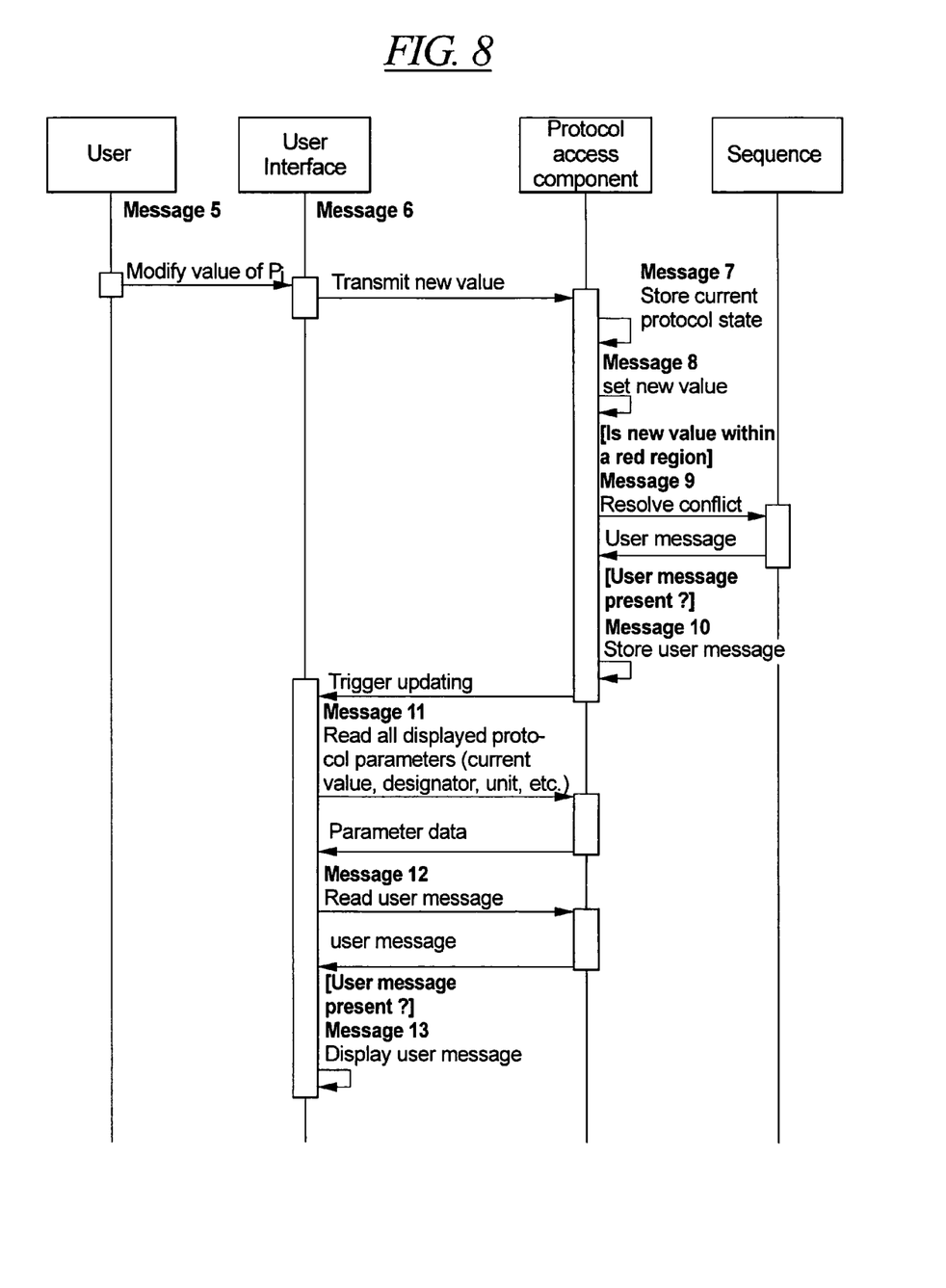
Figure 9:
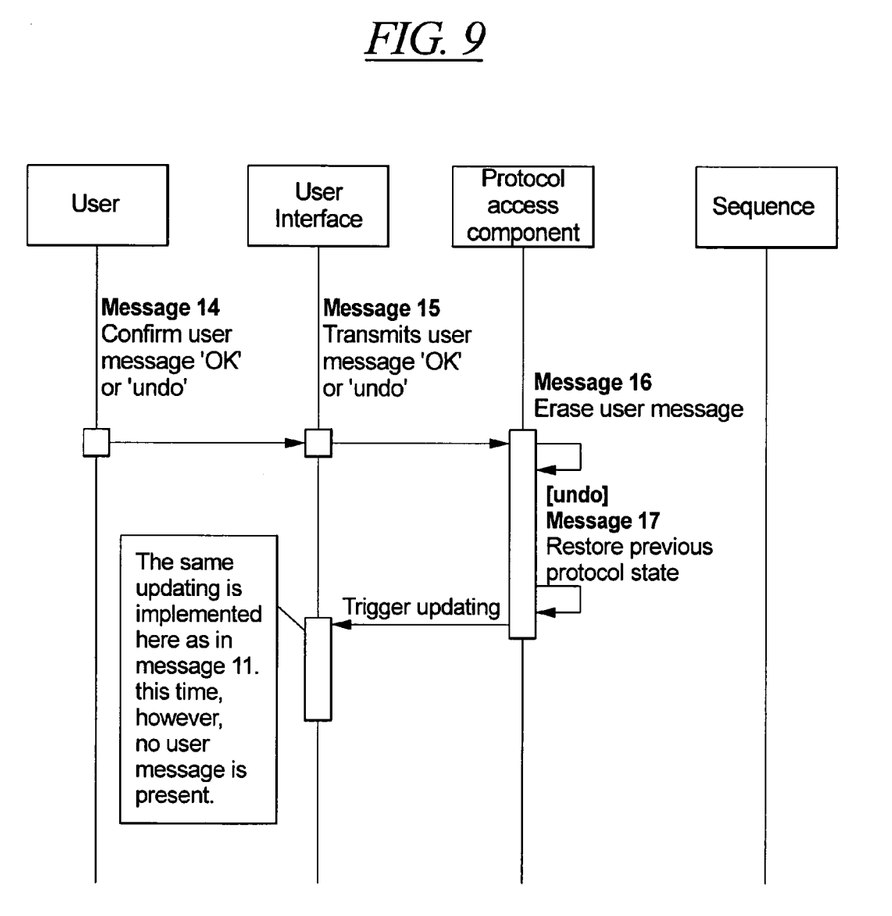

In sequence diagrams, FIGS. 7, 8 and 9 show the cooperation between the operator and the relevant software components during the above described scenario using the inventive method.

Sequence diagrams serve the purpose of representing the chronological sequence of the communication between the involved components. In each diagram, time runs from the top to the bottom. The relevant components are shown by perpendicular life lines. If the life line is covered by a wide perpendicular bar, this means that the component is active in the corresponding time interval. If such a bar is covered by a further laterally offset bar, this indicates a recursive or iterative action. Messages between the individual components are represented by horizontal arrows between the life lines. The answer to a message is represented as a separate arrow (reversed direction). A condition in square brackets on an arrow means that the message (and therefore the appertaining answer as well) is sent only when the condition is fulfilled. A component also be the receiver of its own message.

Apart from the operator, the diagrams of FIGS. 7, 8 and 9 differentiate between the components "user interface", "protocol access component" and "sequence". The user interface is the part of the software with which the user directly communicates. The component sequence represents the portions of the software, which realizes a specific physical measuring method (e.g. spin-echo-sequence, turbo-spin-echo-sequence, etc.). Generally, each of these measuring methods can have individual dependencies between the parameters. The other software components user interface and protocol access component do not "know" which measuring method is realized in the current constellation (and therefore the current parameter dependencies). The other software components merely know a set of standardized entry points in the sequence. Therefore, the sequence can be replaced by any software module which makes these entry points available. The protocol access component is a software layer, which is situated between the user interface and the actual protocol data. Upon request, the protocol access component supplies parameter data to the user interface and may modify (in turn, upon request of the user interface) the protocol data. A communication with the sequence is necessary therefore, particularly for determining the value range and the dependencies. The user interface does not directly communicate with the sequence.

Messages that are exchanged between the components during the above described scenarios are described in the following. The individual messages are referenced by their number in the sequence diagrams of FIGS. 7, 8 and 9.

If the user selects the parameter $P_i$ (message 1), the user interface needs the value range of the parameter in order to display it. The user interface thus requests the value range from the protocol access component (message 2).

The sequence component provides the protocol access component with two methods by means of which the value range can be determined:

The routine "check protocol" can make a Boolean statement for each protocol, i.e. whether this parameter set can be measured.

The routine "solve conflict" is called only when the protocol has been rejected by "check protocol". It has the task of modifying the parameter data such that the protocol can still be measured. If this can be achieved, it answers with TRUE, otherwise the return value is FALSE.

The protocol access component now iteratively modifies the value of the parameter $P_i$ (message 3.n.1, n thereby indicates the iterative step) in a previously fixed interval $\{I_i, I_i+incr_i, I_i+2*incr_i, \ldots, h_i\}$. In every iteration step n, the routine "check protocol" is initially called with the modified parameter set (message 3.n.2). If it accepts the modified protocol, the tested parameter value belongs to the "green" value range of the parameter $P_i$. Otherwise, it is tested with the routine "solve conflict$_i$" (message 3.n.3) i.e., whether the sequence is capable of generating a measurable protocol by adapting other parameters. If this can be achieved, the parameter value belongs to the "red" value range of $P_i$. If the answer of "solve conflict$_i$" is FALSE, the corresponding parameter value is excluded. Prior to the iterative method, the current measurable protocol is stored (message 3.0) and this protocol state is restored after each iterative step (message 3.n.4). If there is no time to test all possible values in the interval (exhaustive search: $(h_i-I_i)/incr_i$ iterative steps), the range limits can be found in approximately $\log2((h_i-I_i)/incr_i)$ iterative steps with the aid of an interval nesting method, for example. The last method functions, however, only when specific assumptions about the value range can be made.

In an earlier initialization phase (not shown in the diagrams), the sequence made the routines "check protocol" and "solve conflict$_i$" known to the protocol access component. The initialization phase thereby corresponds to one of the aforementioned entry points into the sequence. It should be pointed out that the routine "check protocol" tests the parameter set as a whole and therefore is independent of the parameter whose value range is to be found. The routine "solve conflict$_i$", by contrast, is parameter-specific (alternatively, the routine "solve conflict$_i$" could be provided with information as to which parameter has been modified). Otherwise, the sequence can solve the conflict by modifying the value of $P_i$ itself (e.g. to the value prior to the iteration start). In MRease, the routines "check protocol" and "solve conflict$_i$" are global C++ functions with a defined interface. Furthermore, an unambiguous character string is allocated to each parameter $P_i$. During the initialization phase, the sequence calls a register function and provides it with the address of the function "solve conflict$_i$" together with the character string, which is allocated to the parameter $P_i$. The addresses of the functions are stored in the protocol access component and are called if required.

After the iterative method has been completed, the protocol access component supplies the value range $A_i$ (as the answer to message 2) to the user interface. The user interface initializes the value display (message 4) and waits for further messages of the user.

If the user now changes the value of the parameter $P_i$ (message 5), the user interface forwards the new value to the protocol access component (message 6). The protocol access component stores the current state of the protocol (message 7), and modifies the value of the parameter $P_i$ in the protocol data (message 8). If the new value of the parameter $P_i$ is situated in the red range, the routine "solve conflict$_i$" is called again for adapting the dependent parameters. In MRease, the function "solve conflict$_i$" is thereby informed of the context (determination of the value range or input of a new value by the user) in which the function is called by means of a transfer parameter. In the context "user input", it must supply additional information, which is necessary in order to format the text for the pop-up function. Furthermore, the calculations are normally more complicated in this context. In the above example, the minimal TR must be determined in the context "user input" given 12 slices. In the context "value range determination", it is sufficient to make a decision whether the protocol can be measured by adapting TR. The actual value of TR is not relevant in this context. The protocol access component stores the text formatted with the function "solve conflict$_i$" for the pop-up dialog (message 10) and, with the response to message 6, initializes an updating of all currently displayed parameters (message 11). This is necessary, since the user interface and the protocol access component do not know which of the parameters have been adapted by the sequence and therefore all of the displayed parameters generally could have changed. If all parameter data have been read, the user interface asks whether a message is present (message 12) and shows the message, if present, in a modal dialog (message 13). Now, the user interface waits for a decision of the user.

The user will now press the "OK" or the "Undo" button command (message 14). The user interface informs the protocol access component of the decision (message 15). If the user has selected the button command "Undo", the protocol access component restores the protocol state again that is stored by message 7. (message 17). The stored user message is deleted (message 16). In the "Undo" case, the response to message 15 initiates a new updating of the displayed parameters. For this purpose, the same steps are carried out in the user interface as during the processing of the response to message 6. This time, however, there is no user message due to message 16 and the method is completed after the parameter data have been read.

The user interface now waits for the next user action.

It should be additionally mentioned that FIGS. 7, 8 and 9 only show the actual flow diagram in MRease in a simplified manner. The actual implementation includes additional steps for the runtime optimization. For example, the iterative method for determining the value range $A_i$ of the parameter $P_i$ is only repeated when $A_i$ is requested by the user interface and when at least the value of one parameter $P_j(j\neq i)$ has changed since the last request. In particular, this is the case when the value of $P_i$ itself has been set in the red range after the last request. Furthermore, the sequence can intervene into the behavior of the user interface by means of registering further optional callback functions, which are called in a defined context. These functions can enable each sequence, for example, to dynamically fade-in or out individual parameters (i.e. dependent on the current protocol state) in the user interface, and/or to prescribe arbitrary, even incoherent value ranges, without a time-intensive exhaustive search, and/or to adapt further parameters without the confirmation of the user given the placing of a parameter, and or to exchange designator, unit, tool tip of the parameter, and/or to fade-in new parameters in the user interface.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for altering a protocol in a magnetic resonance apparatus comprising the steps of:
   (a) displaying a display presentation at a user interface for a magnetic resonance apparatus containing a first parameter in a protocol for operating the magnetic resonance apparatus to obtain magnetic resonance data and a second parameter in said protocol for operating the magnetic resonance apparatus;

(b) in said display presentation, showing a range of values for said first parameter including designating a first sub-range within said range wherein selection of a value does not modify said second parameter, and a second sub-range within said range wherein selection of a value causes modification of said second parameter;

(c) if a value for said first parameter is selected in said second sub-range, automatically showing in said display presentation how the value selected for said first parameter will modify said second parameter; and (d) giving a user an option in said display presentation to confirm selection of said value selected for said first parameter or to reject selection of said value selected for said first parameter, via said user interface.

2. A method as claimed in claim 1 wherein step (c) comprises automatically showing how the value selected for said first parameter will modify said second parameter in a pop-up dialog within said display presentation.

3. A method as claimed in claim 1 wherein step (b) comprises designating said first sub-range with a first color in said display presentation and designating said second sub-range with a second color in said display presentation.

* * * * *